United States Patent [19]
Rusink

[11] Patent Number: 5,522,876
[45] Date of Patent: Jun. 4, 1996

[54] SCREW-IN PACING LEAD

[75] Inventor: Gerrit J. Rusink, Gaanderen, Netherlands

[73] Assignee: Vitatron Medical, B.V., Dieren, Netherlands

[21] Appl. No.: 329,233

[22] Filed: Oct. 26, 1994

[51] Int. Cl.⁶ ............................... A61N 1/05; A61B 5/04
[52] U.S. Cl. .................. 607/127; 607/126; 607/128; 607/122
[58] Field of Search ................... 607/126, 127, 607/128, 130, 131

[56] References Cited

U.S. PATENT DOCUMENTS

| | | | |
|---|---|---|---|
| 3,974,834 | 8/1976 | Kane | 128/418 |
| 4,046,151 | 9/1977 | Rose | 128/404 |
| 4,566,467 | 1/1986 | DeHaan | 128/784 |
| 4,827,940 | 5/1989 | Mayer et al. | 128/642 |
| 4,876,109 | 10/1989 | Mayer et al. | 427/2 |
| 4,913,147 | 4/1990 | Fahlstrom et al. | 128/419 P |
| 5,259,394 | 11/1993 | Bens | 607/127 |
| 5,374,287 | 12/1994 | Rubin | 607/131 |
| 5,378,239 | 1/1995 | Termin et al. | 604/104 |
| 5,411,546 | 5/1995 | Bowald et al. | 607/126 |

*Primary Examiner*—William E. Kamm
*Assistant Examiner*—Carl H. Layno
*Attorney, Agent, or Firm*—Woodcock Washburn Kurtz Mackiewicz & Norris

[57] ABSTRACT

A lead for use with a pacemaker in a pacing system, the lead having at least one electrode placed at its distal tip and a helical fixation member at the lead distal tip for screwing the lead into a patient's heart wall. The helical member is composed of shape-memory metal and until use is encapsulated in a shrunken state with a diameter less than the diameter of the lead casing. The encapsulation material is preferably mannitol or a like material which dissolves when placed in the human heart. The shape-memory helix when released from the encapsulation material assumes an expanded diameter, greater than electrode diameter and preferably greater, so that when it is screwed into the heart wall, the helical coils are displaced radially away from the outer edge of the tip electrode. By this design, the damage to the heart tissue caused by the helix does not affect the heart wall immediately proximate to the tip electrode.

4 Claims, 1 Drawing Sheet

SCREW-IN PACING LEAD

BACKGROUND OF THE INVENTION

1. Field of the Invention

The present invention is directed to leads to be used in cardiac pacemaker systems and, particularly, pacing leads having screw-in-type fixation members at the distal end thereof.

DESCRIPTION OF THE PRIOR ART

As is well known, in cardiac pacing systems it is desirable to securely fix, or anchor the distal end of the pacing lead to the heart wall so as to optimize reliable transmission of stimulation pulses to the heart wall. Many pacing systems utilize a lead with a passive anchoring means, such as tines, which are located at the distal end of the lead, relying on the growth of the trabeculae into and around the tines with time in order to hold the distal end securely in place with respect to the heart wall. Other leads use more active fixation members, such as bristles, hooks, wires, and in particular screw, or helical members. In practice, when a screw-in type lead has been introduced through a vein into the heart, the physician positions the helical fixation member against the heart wall and then rotates the helix so that it screws into the heart wall. This sort of active, or traumatic fixation results in scarring of the heart wall at the point where the helix enters and rotates, which scaring can adversely affect the transmission of signals between the tip electrode and the heart. Since the helix is aligned substantially axially with the center longitudinal axis of the lead, the scarred area is found approximately in a circle around the distal end of the lead. It can be seen that if the diameter of this helical circle is within the outer diameter of the distal tip electrode, the scarred tissue is directly proximate to the electrode, which adversely affects efficient signal transmission. On the other hand, if the helical diameter is greater than and displaced outwardly from the electrode, then the scarring caused by the trauma of the helix is substantially less of a problem.

Prior art pacing leads having been designed to meet many of the problems posed by helical or screw-in fixation elements. For example, U.S. Pat. Nos. 3,974,834 and 4,046,151, assigned to Medtronic, Inc., show screw-in electrodes where the anchor helix element is released after insertion of the lead tip into the heart. This avoids the problem of the sharp helical member being exposed as the lead is passed through a vein into the heart. Further, it is known to provide a soluble covering for the anchor mechanism. See U.S. Pat. Nos. 4,827,940 and 4,876,109, which show a number of different configurations of a soluble covering for a distal screw-in-type lead.

The use of shape-memory metal components is also known in the pacing art. The patent to Fahlstrom et al. No. 4,913,147, discloses the use of memory metal components at both the distal and proximal ends, as well as within an intermediate section lead. Certain embodiments of this patent show the use of a memory metal for expanding tines after the distal end of the lead has been placed in the heart. Other illustrated embodiments show the use of a memory metal component to release the anchor element so that it can be fixated into the heart, to force the helix out so that it is exposed, and to provide different configurations for fixation of the anchor element itself.

However, none of the known prior art arrangements address the aforementioned problem caused by trauma to the heart wall in the area of the distal tip electrode. It is accordingly an object of this invention to provide a pacing lead with a helical fixation element which provides the advantages of a screw-in-type element, but which avoids the disadvantages caused by trauma in the vicinity of the distal tip pacing electrode.

SUMMARY OF THE INVENTION

The above prior art problem is addressed in accordance with the present invention in a cardiac pacing lead, wherein the lead has at its distal end a memory helix made of shape-memory metal. The helix is initially encapsulated so that it is constrained in a shrunken state in which its diameter is substantially less than the diameter of the lead casing. The helix is preferably encapsulated by mannitol or like material which dissolves once the lead is in the patient's heart. Upon dissolution of the mannitol, the helix assumes a diameter greater than the diameter of the tip electrode, preferably somewhat greater than the diameter of the lead casing. After the expansion of the helix, the physician screws the helix into the heart wall with the great portion of the trauma to the heart wall being radially outside and away from the tip electrode which is directly proximate to the heart wall.

DESCRIPTION OF THE PREFERRED EMBODIMENTS

Figure 1:
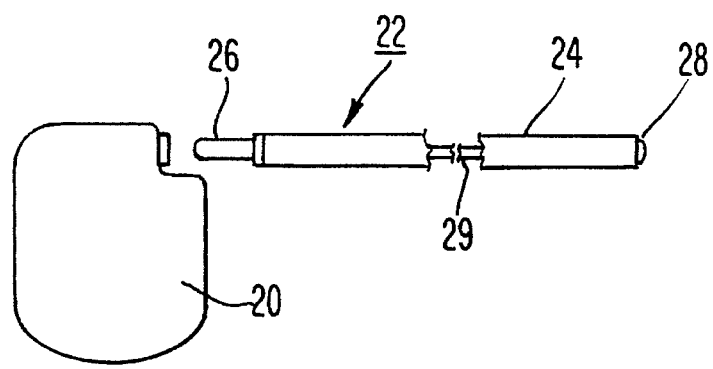
FIG. 1 is a schematic representation of a lead in accordance with this invention, together with a cardiac pacemaker, the lead and pacemaker together providing a cardiac pacing system.

Referring now to FIG. 1, there is shown a pacing system comprising a pacemaker 20 and a lead 22. As illustrated, the lead 22 has a substantially cylindrical tube 24, having an outer tube casing of a first diameter $D_1$. One or two conductors 29, depending upon whether the system is unipolar or bipolar, run the length of the lead through the tube 24, and connect between the proximal end 26 and the distal end 28. The proximal end 26 is configured to be mechanically and electrically connected to the pacemaker 20, while the distal end 28 carries at least one electrode 30 (FIG. 2A) to which a conductor 29 is attached.

Figure 2A:
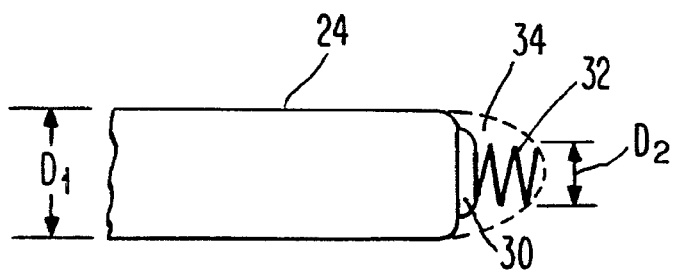
FIG. 2A is a representation of the distal end portion of a lead in accordance with this invention, wherein the helical anchor element remains encapsulated in a shrunken state.
Figure 2B:
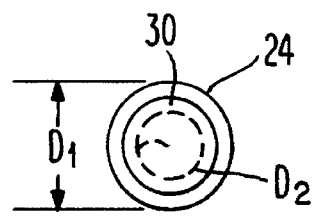
FIG. 2B is an end view of the FIG. 2A configuration.

Referring now to FIGS. 2A and 2B, a distal end portion of the lead is shown, having an electrode 30 positioned at the distal tip end of the tube 24. The electrode 30 may be of different known configurations, but it is generally aligned axially with the length of the tube casing 24, i.e., it is substantially circular having its center axis in line with the center axis of the lead casing. A helix element 32 is shown extending distally from the tip end, and having a shrunken diameter $D_2$. The helix is constrained in a shrunken condition by an encapsulating material 34, suitably mannitol, which is shaped to provide a smooth forward end, thereby facilitating entry of the lead through the patient's vein. As seen in FIG. 2B, in a shrunken state the diameter $D_2$ of the helix (shown by the dashed line) is less than the diameter $D_1$ of the electrode, which diameter in turn is less than the diameter $D_1$ of the casing.

Figure 3A:
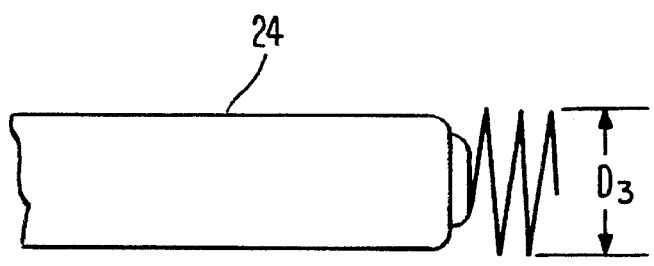
FIG. 3A is a representation of the distal end portion of the same lead of this invention, wherein the encapsulating material has dissolved and the helical element has assumed an expanded state with a diameter greater than the diameter of the tip electrode.
Figure 3B:
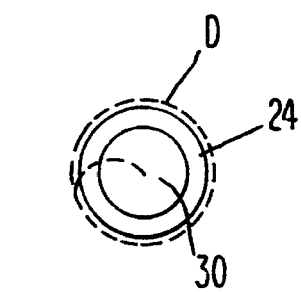
FIG. 3B is an end view of the FIG. 3A configuration.

Referring now to FIG. 3A, the same lead is shown in a condition where the encapsulating material 34 has dissolved away, due to the lead having been placed within the patient's heart. In this situation, the helix has expanded through to its remembered state, such that its outer diameter is illustrated as $D_3$, which is clearly greater than the outer diameter of the electrode 30. It is in this state that the helix is screwed into the patient, and the cross-sectional illustration of FIG. 3B shows that the trauma to the heart wall caused by the helix is substantially displaced from the immediate area of the electrode. In practice, and by way of illustration, the casing diameter D1 may be 1.0 or 2.0 ram; the tip electrode has a diameter of 0.85 or 1.7 mm.

The fixation element may be made of any one of the suitable shape memory alloys that are commercially available. The fixation element need not be perfectly helical, and is within the scope of the invention so long as it expands radially away from the tip electrode. While the expanded diameter $D_3$ is shown as being greater than tube diameter $D_2$, it need not be greater than $D_1$, but should definitely be greater than the electrode diameter. The diameter $D_2$ of the helix in the shrunken state should preferably be less than the electrode diameter, but $D_2$ is somewhat controlled by fabrication concerns. It is also noted that the lead of this invention may be unipolar or bipolar, and in either case the improvement relates to the relationship of the screw-in member to the tip electrode. Likewise, the tip electrode may not be precisely circular, but in any event has an effective diameter to which the helix is compared.

What is claimed is:

1. A lead for use with a pacemaker in a pacemaker system, having a proximal end for attachment to said pacemaker and a distal end having an electrode at the tip thereof, said electrode having a first diameter, a substantially cylindrical tube running the length of said lead between said proximal and distal ends, said tube having a second diameter greater than said first electrode diameter, conductor means within said tube length for conducting electrical signals between said proximal end and said tip electrode, and screwtype fixation means connected to said distal end for anchoring said distal end into a patient's heart, said fixation means further comprising a helix having memory metal, a coating encapsulating said helix and holding it in a state such that it has a third diameter less than said second body diameter, said coating comprising a material which dissolves when placed in file human heart, said helix expanding to a greater diameter than said tube second diameter when said coating dissolves and releases said helix.

2. The lead as described in claim 1, wherein said coating is temperature sensitive.

3. The lead as described in claim 1, wherein said coating comprises mannitol.

4. The lead as described in claim 1, wherein said helix and said electrode are aligned substantially concentrically with the axis of said cylindrical tube.

\* \* \* \* \*